US012059673B2

(12) United States Patent
Bellamy

(10) Patent No.: US 12,059,673 B2
(45) Date of Patent: Aug. 13, 2024

(54) METHOD FOR CONVERTING AN ORGANIC MATERIAL INTO A CATALYST FOR BIOLOGICAL HYDROSYNTHESIS

(71) Applicant: VRM International Pty Ltd, Bohle (AU)

(72) Inventor: Kenneth Michael Bellamy, Townsville (AU)

(73) Assignee: VRM International Pty Ltd, Bohle (AU)

( * ) Notice: Subject to any disclaimer, the term of this patent is extended or adjusted under 35 U.S.C. 154(b) by 523 days.

(21) Appl. No.: 17/472,854

(22) Filed: Sep. 13, 2021

(65) Prior Publication Data

US 2023/0082338 A1  Mar. 16, 2023

(51) Int. Cl.
| | | |
|---|---|---|
| *C12P 1/00* | (2006.01) | |
| *B01J 35/27* | (2024.01) | |
| *B01J 37/36* | (2006.01) | |
| *B09B 3/60* | (2022.01) | |

(Continued)

(52) U.S. Cl.
CPC ............... *B01J 37/36* (2013.01); *B01J 35/27* (2024.01); *B09B 3/60* (2022.01); *B09C 1/10* (2013.01); *C09K 17/14* (2013.01); *C12P 1/00* (2013.01)

(58) Field of Classification Search
CPC ............. C12P 1/00; B09C 3/60; B09B 101/70
See application file for complete search history.

(56) References Cited

U.S. PATENT DOCUMENTS

| | | |
|---|---|---|
| 4,052,818 A | 10/1977 | Hagerty |
| 6,497,534 B1 | 12/2002 | McCoy |
| 6,719,902 B1 | 4/2004 | Alvarez et al. |

(Continued)

FOREIGN PATENT DOCUMENTS

| | | | |
|---|---|---|---|
| AU | 2012283757 A1 | 1/2014 | |
| AU | 2014250680 A1 * | 5/2015 | ............. C05F 15/00 |

(Continued)

OTHER PUBLICATIONS

Australian Examination Report for Australian Application No. 2020203536, dated Jun. 23, 2022, 7 pages.

(Continued)

*Primary Examiner* — Rip A Lee
(74) *Attorney, Agent, or Firm* — Cooper Legal Group LLC

(57) ABSTRACT

Method for converting organic material into catalyst for biological hydrosynthesis, comprising providing organic material comprising at least one source of readily available carbon, at least one complex carbon-containing compound and at least one source of protein and contacting the organic material with preparatory catalyst is provided. The organic material is subjected to a size reduction process to produce size-reduced organic material and a solid to liquid ratio of the size-reduced organic material is adjusted to form organic material slurry. The organic material slurry is subjected to a fermentation process to produce amended organic material, by applying a process catalyst to at least a portion of the organic material slurry. A liquid is recovered from the amended organic material and transferred to a fermentation chamber, where it is subjected to a fermentation process to produce amended liquid by applying balancing catalyst to the liquid. The amended liquid is the catalyst.

16 Claims, 1 Drawing Sheet

(51) Int. Cl.
*B09C 1/10* (2006.01)
*C09K 17/14* (2006.01)

(56) References Cited

U.S. PATENT DOCUMENTS

| | | | |
|---|---|---|---|
| 6,770,198 B2* | 8/2004 | Newton | C02F 3/10 |
| | | | 210/615 |
| 6,773,592 B2* | 8/2004 | Bellamy | C02F 3/10 |
| | | | 210/615 |
| 7,455,774 B2 | 11/2008 | Chandraghatgi et al. | |
| 7,585,132 B2 | 9/2009 | Imbrie | |
| 8,114,659 B2 | 2/2012 | Rawson et al. | |
| 8,689,819 B2 | 4/2014 | Hashimoto et al. | |
| 9,034,633 B2 | 5/2015 | Kumar et al. | |
| 9,175,258 B2 | 11/2015 | Bywater-Ekegard et al. | |
| 9,212,358 B2 | 12/2015 | Razavi-Shirazi et al. | |
| 10,004,188 B2 | 6/2018 | Williams et al. | |
| 10,531,615 B2 | 1/2020 | Jimenez Santillana et al. | |
| 10,906,075 B2 | 2/2021 | Franssen et al. | |
| 10,973,184 B1 | 4/2021 | Yin | |
| 11,623,257 B2* | 4/2023 | Bellamy | B09C 1/08 |
| | | | 405/128.75 |
| 11,865,596 B2* | 1/2024 | Bellamy | B09C 1/08 |
| 2002/0088177 A1 | 7/2002 | Gergek | |
| 2004/0182780 A1* | 9/2004 | Lee | C05G 5/20 |
| | | | 210/612 |
| 2005/0000903 A1 | 1/2005 | Mecs et al. | |
| 2006/0130546 A1 | 6/2006 | Beaton et al. | |
| 2010/0227381 A1 | 9/2010 | Hoag et al. | |
| 2012/0085024 A1 | 4/2012 | Leung | |
| 2014/0329677 A1 | 11/2014 | Anisimova et al. | |
| 2015/0093199 A1 | 4/2015 | Borden et al. | |
| 2017/0305804 A1 | 10/2017 | Ayers et al. | |
| 2019/0297799 A1 | 10/2019 | Larue | |
| 2020/0079672 A1 | 3/2020 | Noland | |
| 2021/0368691 A1* | 12/2021 | Bellamy | B09C 1/08 |

FOREIGN PATENT DOCUMENTS

| | | | | |
|---|---|---|---|---|
| CN | 1269738 A | | 10/2000 | |
| CN | 1413963 A | | 4/2003 | |
| CN | 103408360 A | * | 11/2013 | ............... C05F 1/00 |
| CN | 106914484 A | | 7/2017 | |
| CN | 107646227 A | | 2/2018 | |
| CN | 107841313 A | | 3/2018 | |
| CN | 108934251 A | | 12/2018 | |
| CN | 109679662 A | | 4/2019 | |
| CN | 110125169 A | | 8/2019 | |
| CN | 110252798 A | | 9/2019 | |
| CN | 110326462 A | | 10/2019 | |
| CN | 110483215 A | * | 11/2019 | ............. A01C 21/00 |
| CN | 111153742 A | * | 12/2019 | ............... C05G 3/60 |
| CN | 210017104 U | | 2/2020 | |
| CN | 113728747 A | * | 12/2021 | ............. A01B 79/00 |
| EP | 2856859 B1 | | 7/2016 | |
| JP | 2003325052 A | | 11/2003 | |
| KR | 101363010 B1 | | 2/2014 | |
| WO | WO 2013/006912 A1 | * | 1/2013 | ............... B09B 3/00 |

OTHER PUBLICATIONS

Chang, et al.: "Effect of different types of organic fertilizers on the chemical properties and enzymatic activities of an Oxisol under intensive cultivation of vegetables for 4 years", Soil Science and Plant Nutrition (2008) 54, 587-599, 13 pages.

Australian Examination Report for Australian Application No. 2020203537, dated Aug. 5, 2022, 5 pages.

Chinese Office Action for Chinese Application No. 202010475251.0, dated Aug. 2, 2022, 15 pages.

Australian Examination Report for Australian Application No. 2020203535, dated Aug. 5, 2022, 5 pages.

CNIPA Office Action for Chinese Application No. 202010476944.1, dated Jun. 6, 2022, 16 pages.

\* cited by examiner

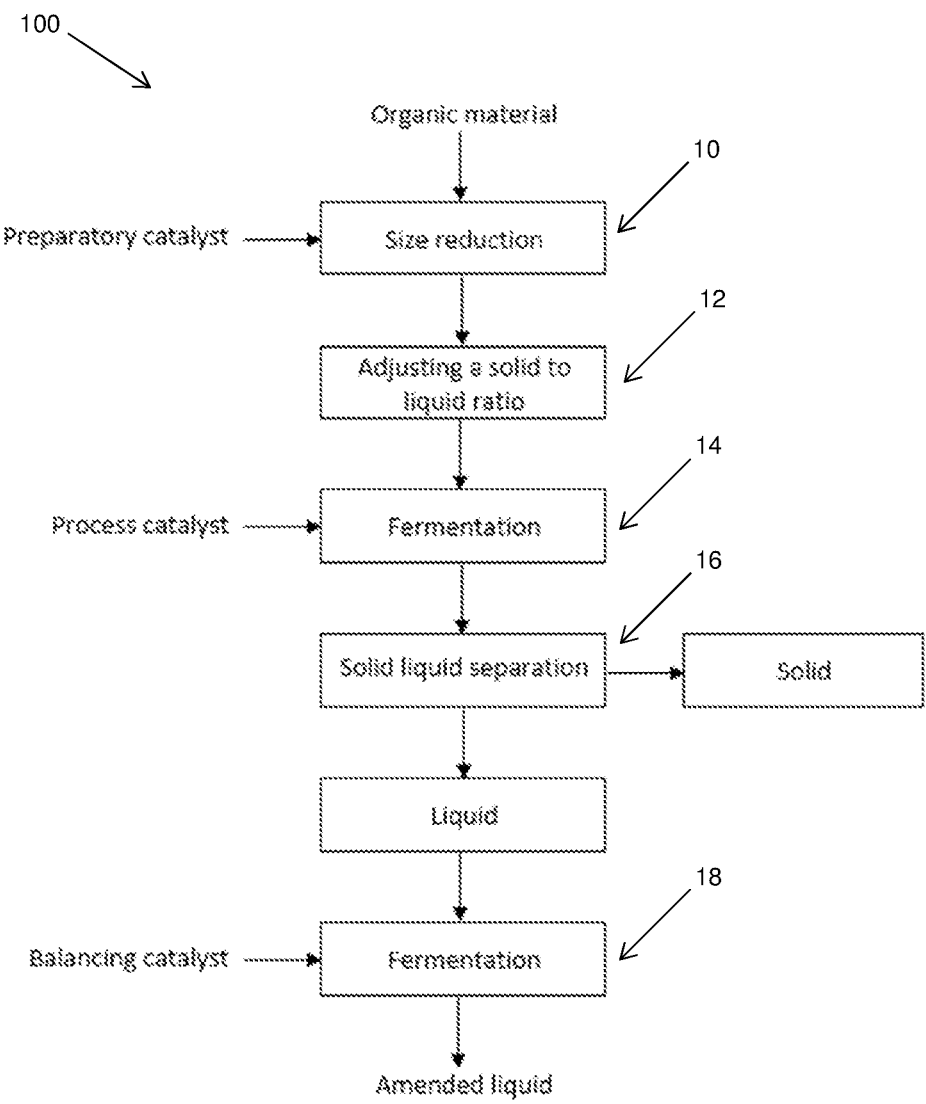

METHOD FOR CONVERTING AN ORGANIC MATERIAL INTO A CATALYST FOR BIOLOGICAL HYDROSYNTHESIS

TECHNICAL FIELD

The present invention relates to a method for converting an organic material into a catalyst for biological hydrosynthesis.

BACKGROUND

Traditional methods of handling and conversion of organic materials depend primarily upon the degradation of the material either naturally, or in a fostered or managed process resulting in wholesale loss of nutrient content and other benefits of material. As a result, the by-products of such conversion processes are typically low in nutrients, reactives or other values and therefore have a low commercial value.

Typically, processes for organic conversion of putrescible material also require, or involve, the incorporation or buy-in of other materials (including inert cellulose or carbon rich materials, nitrogen rich elements, etc); and energy in the form of mechanical manipulation, heat or other input in order to provide a balanced nutrient stock from which to allow or foster the degradation of the material concerned. This aspect of conventional processes increases the volumetric load on facilities, the cost of process and the footprint required and adds a risk of mismanagement to processes which may all work to reduce the commercial viability of the conversion process. In addition, many of the prior art processes are batch operated processes and/or constrained by the capacity of the equipment involved. Such handling methods have also been limited by the production of various gases and other substances which are a by-product of the processes themselves. In particular, processes which seek to digest, degrade, or reduce an organic residue typically produce one or more greenhouse gases and also commonly produce harmful gases such as hydrogen sulphide and ammonia which require specific management of ecological footprint during processing.

It will be clearly understood that, if a prior art publication is referred to herein, this reference does not constitute an admission that the publication forms part of the common general knowledge in the art in Australia or in any other country.

SUMMARY OF INVENTION

Embodiments of the present invention provide a method for converting an organic material into a catalyst for biological hydrosynthesis, which may at least partially address one or more of the problems or deficiencies mentioned above or which may provide the public with a useful or commercial choice.

The term "catalyst" as used herein is broadly defined as a substance that produces or generates a reaction regardless of whether it undergoes a change itself.

The term "amendment" as used herein is broadly defined as a process or action that leads to a change in the condition of an organic material, including a physical change, a chemical change, a biological change, or any suitable combination thereof. In this instance, it will be understood that amending an organic material and/or a liquid recovered resulting from a process which incorporates amendment and conversion of the organic material in effect amends the three-dimensional space including the surface of the organic material and/or the liquid, the contiguous atmosphere about the organic material and/or the liquid and the three-dimensional volume of the organic material and/or the liquid below the surface of the organic material and/or the liquid.

With the foregoing in view, the present invention in one form, resides broadly in a method for converting an organic material into a catalyst for biological hydrosynthesis, the method comprising the steps of:

providing an organic material comprising at least one source of readily available carbon, at least one complex carbon-containing compound and at least one source of protein;

contacting the organic material with a preparatory catalyst;

subjecting the organic material to a size reduction process to produce a size-reduced organic material;

adjusting a solid to liquid ratio of the size-reduced organic material to form an organic material slurry;

subjecting the organic material slurry to a fermentation process to produce an amended organic material, by applying a process catalyst to at least a portion of the organic material slurry;

recovering a liquid from the amended organic material and transferring the liquid recovered to a fermentation chamber, and subjecting the liquid recovered to a fermentation process to produce an amended liquid by applying a balancing catalyst to the liquid recovered in the fermentation chamber, wherein the amended liquid is a catalyst for biological hydrosynthesis.

Advantageously, the present invention enables the conversion of an organic matter (such as waste food, or putrescent organic material) into a catalyst for biological hydrosynthesis and enables the conversion of an organic matter into a catalyst for biological hydrosynthesis without the wholesale release of greenhouse gases such as methane, water vapour, nitrous oxide or other nitrogen compounds, hydrogen sulphide or other sulphide compounds, and carbon dioxide. In addition, the present invention provides a method for the conversion or organic material to a useful product (such as a bio-fertiliser, or the like) which is not limited by the processing capacity of the equipment involved. In addition, the process prevents a fermented liquor from putrefying, improving the shelf life of the resultant product and enables the production of a single stabilised catalyst for soil amendment from any form of putrescent organic material regardless of its origin.

The present invention provides a method for converting an organic material into a catalyst for biological hydrosynthesis. In a preferred embodiment, the present invention provides a method for the continuous fermentation of an organic material which converts the organic material into a catalyst for biological hydrosynthesis. Preferably, the present invention provides a method for the continuous fermentation of an organic material which converts the organic material into a liquid bio-fertiliser.

The catalyst for biological hydrosynthesis may be used for any suitable purpose.

For instance, the catalyst for biological hydrosynthesis may be used as a catalyst in a fermentation process, to amend an organic material, to amend a liquid recovered from a fermentation process, or the like.

For instance, the catalyst for biological hydrosynthesis may be used to amend a growth media, such as a soil, clay, sand, vermiculite, perlite, coir, potting mix, composted bark, decomposed granite, sphagnum peat moss, straw, or the like.

For instance, the catalyst for biological hydrosynthesis may be used to amend a site, such as arable land, non-arable land, pasturable land, meadows, grassland, agricultural land, farmland, orchards, plantations, forests, bush or scrub land, park land, residential land, golf courses, athletics fields, race courses, wetlands, water courses and bodies, land-based aquaculture facilities, rehabilitation sites, remediation sites, restoration site, revegetation site, fire-affected sites, mine sites, landfill, waste dumps, commercial composting facilities, on-farm composting facilities, or the like.

For instance, the catalyst for biological hydrosynthesis may be used to amend a nutrient depleted site, a contaminated site, or the like. For instance, the catalyst for biological hydrosynthesis may be used in waste treatment, such as treatment of solid waste material, liquid waste material, waste water, or the like.

In some embodiments, the method for converting an organic material into a catalyst for biological hydrosynthesis comprises providing an organic material comprising at least one source of readily available carbon, at least one complex carbon-containing compound and at least one source of protein.

Any suitable organic material may be used in the method. For instance, vegetable matter (including fruits, vegetables, pulses, grains, grasses etc.) or animal matter may be used. The organic material may be fresh organic material, food scraps, waste material (including rotting food or other organic material) or the like, or a combination thereof. Preferably, the organic material may comprise fermentable material.

Preferably, the organic material comprises at least one source of readily available carbon. For instance, the at least one source of readily available carbon may comprise a source of a sugar (such as molasses), a source of a hydrocarbon, a source of a lipid, or the like.

In preferred embodiments, the source of readily available carbon may be at least partially sourced from an amended organic material. Any source of amended organic material may be used. For instance, the amended organic material may be the amended organic material produced according to the method of the present invention, may be a sediment separated from the liquid recovered from the amended organic material, may be a sediment separated from the amended liquid, or any suitable combination thereof.

Preferably, the organic material comprises at least one complex carbon-containing compound. Complex carbon-containing compounds, such as polysaccharides and modified polysaccharides, are carbon-containing compounds which are large and have a complex and highly specific structure. For instance, the at least one complex carbon-containing compound comprises a source of a chitin, a source of a chitosan, a source of a cellulose, a source of a hemicellulose, a source of a lignin, a hydrocarbon, or the like.

Preferably, the organic material comprises at least one source of a protein. For instance, the at least one source of a protein may comprise an animal by-product material (such as an animal carcass, bone, fat, connective tissue, offal, blood, feathers, hair, fur, skin, horns, hooves, or the like), an animal manure or urine, a dairy waste material (such as whey, curds, or the like).

The organic material may be contacted with a preparatory catalyst. Typically, the organic material may be contacted with a preparatory catalyst through contact with equipment (such as macerators, agitators, containers, bins, buckets, conveyors, and the like) cleaned with the preparatory catalyst. In this instance, it will be understood that residual preparatory catalyst on the surface of the equipment may be transferred to the organic material during processing of the organic material.

For instance, residual preparatory catalyst on a surface of a blade of a size reduction means may be transferred to the organic material during size reduction of the organic material.

For instance, residual preparatory catalyst in the bottom of a bin configured to contain the organic material therein may be transferred to the organic material during storage.

For instance, residual preparatory catalyst on a surface of the fermentation chamber may be transferred to the organic material slurry during fermentation.

In use, it is envisaged that the preparatory catalyst may advantageously promote desired biological reactions and remove residual materials from surfaces, thus restricting the proliferation of competitive fermentative or putrescent microbial activity in and around the process. In use, it is envisaged that the removal of residual materials from a surface by the preparatory catalyst may expose associated microorganisms to the preparatory catalyst, controlling their proliferation in and around the process.

Any suitable preparatory catalyst may be used.

Preferably, the preparatory catalyst may comprise an essential oil or extract. Any suitable type of essential oil or extract may be used. For instance, the essential oil or extract may comprise an oil obtained from the skin or peel of a fruit (such as lemon, lime, orange, citrus, garcinia, or the like), flowers (such as peony, or the like), leaves (such as pandan, lemongrass, pine, eucalyptus, or the like), seeds, or any suitable combination thereof. Preferably, the preparatory catalyst may comprise an essential oil or extract comprising citrus, pinene, limonene, cineole, terpinenol, or the like.

The effective application rate of the preparatory catalyst through contact with the organic material may be any suitable rate. In this instance, it will be understood that the effective application rate is intended to refer to the amount of preparatory catalyst which is effectively applied to the organic material as a result of contact of the organic material with equipment cleaned with the preparatory catalyst.

For instance, the effective application rate may be about 0.5 L per 1000 L of organic material, about 1 L per 1000 L of organic material, about 5 L per 1000 L of organic material, about 10 L per 1000 L of organic material, about 25 L per 1000 L of organic material, about 50 L per 1000 L of organic material, about 75 L per 1000 L of organic material, about 100 L per 1000 L of organic material, about 150 L per 1000 L of organic material, about 200 L per 1000 L of organic material, or about 250 L per 1000 L of organic material.

However, a person skilled in the art will appreciate that the effective application rate may vary depending on a number of factors, including the type and composition of the organic material, the period of time in which the organic material may be in contact with the preparatory catalyst and the concentration of the preparatory catalyst.

Preferably, the organic material may be contacted with the preparatory catalyst at an effective application rate of about 5 L of preparatory catalyst per 1000 L of organic material.

The organic material may be subjected to a size reduction process to produce a size-reduced organic material. Any suitable size reduction technique may be used.

For instance, the organic material may be crushed, ground, cut, milled, shredded, disintegrated, torn, or the like, or any combination thereof.

The organic material may be subjected to one or more size reduction processes. Any such size reduction processes may be completed in a single or multiple pass operation, which may include one, two, three, four, or any number of size reduction steps, to achieve a desired average particle size.

A person skilled in the art will appreciate that the length of time for which the organic material is subjected to the size reduction process may vary depending on a number of factors including the type of organic material, the volume of organic material, the type of size reduction technique being used, the preferred particle size of the size reduced organic material product and so on.

Although the size reduction process may be used for any organic material, it is envisaged that a size reduction process may be most beneficial where a proportion of the organic material is greater than 5 cm in size (for instance, branches, large bones, animal carcasses etc.).

The solid to liquid ratio of the size-reduced organic material may be adjusted to form an organic material slurry. In this instance, it will be understood that the organic material slurry may comprise a suspension of the size-reduced organic material in the liquid. The solid to liquid ratio of the size-reduced organic material by an adjusted by any suitable means.

For instance, the amount of size-reduced organic material may be increased, a liquid may be added to the size-reduced organic material, liquid may be drained from the size-reduced organic material, the size-reduced organic material may be subjected to a drying and/or dewatering process, or any suitable combination thereof.

In some embodiments, the solid to liquid ratio may be adjusted before, during or after size reduction of the organic material. In this instance, it is envisaged that the addition of liquid may facilitate the size reduction process, may facilitate the transfer of the size-reduced organic material between containers, may facilitate the transfer of a source of and/or substrates produced by and which stimulate the activity of at least one aerobic microorganism, an anaerobic microorganism, a heterotrophic microorganism and a photosynthetic microorganism to the organic material, may facilitate the amendment of the organic material.

In use, it is envisaged that the liquid may facilitate electron transfer in and/or on the size-reduced organic material facilitating the fermentation process.

The ratio of solid to liquid may be any suitable ratio. Preferably, however, the ratio of solid to liquid may be sufficient to form a slurry of liquid and solid components.

For instance, the organic material slurry may comprise at least 25% solid components, at least 30% solid components, at least 35% solid components, at least 40% solid components, at least 45% solid components, at least 50% solid components, at least 55% solid components, at least 60% solid components, at least 65% solid components, at least 70% solid components, at least 75% solid components, at least 80% solid components, at least 85% solid components, at least 90% solid components, at least 95% solid components, or 100% solid components.

In preferred embodiments, the ratio of solid to liquid may form an organic material slurry comprising at least about 25% to 30% solid components. However, again a person skilled in the art will appreciate that the ratio of solid to liquid may vary depending on a number of factors, such as the endogenous moisture content of the organic material, the type and composition of the organic material, the type and composition of the liquid and the maturity of the fermentation process.

Any suitable liquid may be used.

For instance, the liquid may be a liquid recovered during the fermentation of a size-reduced organic material, a liquid prepared from the fermentation of the liquid recovered from the amended organic material, a liquid fertiliser, a source of water, or any suitable combination thereof.

Preferably, however, the liquid may be substantially free of contaminants. For instance, the liquid may be substantially free of chemical contaminants (such as pesticides, herbicides, arsenic, cadmium, chromium, copper, lead, mercury, nickel, selenium, zinc or the like), physical contaminants (such as plastics, glass, rocks, metals, or the like), biological contaminants (such as *Salmonella* spp., faecal coliforms, or the like), or the like.

Preferably, the liquid may be substantially free of copper.

Suitably, the liquid may be substantially free of glycophosphate or glyphosphate. As used herein, statements that a liquid is "essentially free" or "substantially free" of contaminants means that in embodiments the levels of contaminants may be undetectable or substantially undetectable or unmeasurable or unquantifiable using standard measuring techniques.

The size-reduced organic material may be subjected to a fermentation process to produce an amended organic material.

Typically, the method comprises subjecting the organic material slurry to a fermentation process to produce an amended organic material, by applying a process catalyst to at least a portion of the organic material slurry.

The process catalyst may be added to the size-reduced organic material before, during or after the size reduction process.

In this instance, it will be understood that the process catalyst may be added to the organic material during preparation of the organic material for size reduction, prior to commencement of the size reduction process, during the size reduction process, after the size reduction process may be completed, or any suitable combination thereof.

Typically, however, process catalyst may be added to the size-reduced organic material during the size reduction process and before the size reduction process may be completed. However, a person skilled in the art will appreciate that the point of addition of the process catalyst to the organic material during the size reduction process may vary depending on a number of factors, such as the type of size reduction process, the number of passes in the size reduction process, the type and composition of organic material and the type of the process catalyst.

In use, it is envisaged that amending the organic material during the size reduction process results in a random distribution of a source of and/or a substrate produced by and which stimulates the activity of the one or more prokaryotic organisms in the organic material, wherein each contact point between the catalysts and the soil becomes a biological energy generation point.

In some embodiments, the process catalyst may be added to the size-reduced organic material and/or the liquid before, during or after the adjustment of the solid to liquid ratio of the size-reduced organic material. For example, it will be understood that the process catalyst may be added to the size-reduced organic material and/or the liquid before the liquid is added to the size-reduced organic material, may be added to the size-reduced organic material and/or the liquid during the addition of the liquid to the size-reduced organic material, may be added to the organic material slurry during the addition of the liquid to the size-reduced organic material, may be added to the organic material slurry after the solid to liquid ratio has been adjusted, or any suitable combination thereof.

Any suitable process catalyst may be used. Preferably, the process catalysts may comprise a source of and/or a substrate produced by and which stimulates the activity of one or more prokaryotic organisms. In this instance, it is envisaged that the process catalyst may have the capacity to capture non-visible radiation and trigger phototrophic and phospholytic reactions such that the prokaryotic organisms may process the substrate and generate simple sugars.

For example, the prokaryotic organism may comprise one or more species of *Archaea*, one or more species of bacteria, or any suitable combination thereof.

The prokaryotic organism may be anerobic, aerobic, autotrophic, heterotrophic, phototrophic, chemotrophic, chemoautotrophic, photosynthetic, or any suitable combination thereof.

In some embodiments, the prokaryotic organisms may include purple non-sulphur producing heterotrophic photosynthetic bacteria, *Lactobacillus* species, yeasts, *Actinomycetes* species, *Nocardia* species, a ray fungi, plankton, a phototropic, autotrophic, heterotrophic or chemotrophic bacteria, or any suitable combination thereof.

The process catalyst may be applied to the size-reduced organic material in any suitable manner.

For example, the process catalyst may be sprayed onto the size-reduced organic material, the size-reduced organic material may be tumble coated in the process catalyst, the process catalyst may be injected into the size-reduced organic material, the process catalyst may form a solution into which the size-reduced organic material may be dipped or at least partially immersed, the process catalyst may form a solution which is added in-line with the addition of the liquid to form the organic material slurry, the process catalyst may form a solution which is dispersed in the organic material slurry, or any suitable combination thereof.

For example, the process catalyst may be sprayed onto the size-reduced organic material, may be drip irrigated, may be furrow irrigated, may be aerially applied, may be broadcasted or spread, or any suitable combination thereof.

However, a person skilled in the art will appreciate that the method of applying the process catalyst to the size-reduced organic material may vary depending on a number of factors, such as the composition and characteristics of the process catalyst, the method of application, and the type and amount of organic material to be amended.

The process catalyst may be applied at any suitable rate to the organic material slurry.

For instance, the process catalyst may be applied at a rate of about 1 L per 1000 L of organic material slurry, about 5 L per 1000 L of organic material slurry, about 10 L per 1000 L of organic material slurry, about 25 L per 1000 L of organic material slurry, about 50 L per 1000 L of organic material slurry, about 75 L per 1000 L of organic material slurry, about 100 L per 1000 L of organic material slurry, about 150 L per 1000 L of organic material slurry, about 200 L per 1000 L of organic material slurry, or about 250 L per 1000 L of organic material slurry.

Again, it will be appreciated that the application rate may vary depending on a number of factors, including the type and composition of the organic material, the percentage solid components in the organic material slurry and the method of application of the process catalyst. Suitably, the process catalyst may be applied at a rate of about 15 L per 1000 L of organic material slurry.

The process catalyst may be mixed with one or more other substances before the process catalyst may be applied to the organic material. Any suitable substance may be used.

For instance, the substance may act as a processing aid for storage and delivery of the catalyst, may facilitate the application of the catalyst to the organic material, may facilitate the organic material taking up the catalysts, may maintain viability of an organism in the catalyst, increase the available pool of a nutrient in the organic material, may stimulate a targeted response in nutrient accumulation, or the like.

Any suitable additive may be used.

For instance, the additive may comprise an emulsifier, a stabiliser, a wetting agent, a preservative, a surfactant, a mineral, a source of a nutrient, or the like.

For instance, a source of calcium may be added to the catalyst to increase the available calcium in the organic material.

For instance, a source of sugar may be added to the catalyst to improve the fermentative capacity of the organic material.

In some embodiments, the process catalyst may be applied to at least a portion of the organic material. Again, it will be appreciated that the at least a portion of the organic material may include the surface of the organic material, the contiguous atmosphere above the organic material and the three-dimensional volume of the organic material below the surface of the organic material.

Any suitable portion of the organic material may be amended.

For instance, the process catalyst may be applied to about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95% or even about 100% of the organic material by volume.

In use, it is envisaged that the size-reduced organic material may be transferred to a container for fermentation. The size-reduced organic material may be transferred to the container before, during or after the solid to liquid ratio of the size reduced organic material is adjusted.

In some embodiments, the size-reduced organic material may be transferred to the container after the process catalyst is applied to the size-reduced organic material and/or the organic material slurry.

The transfer of the size-reduced organic material and/or the organic material slurry may be achieved using any suitable technique.

For example, the material may be fed under gravity, may be transferred using mechanical means (such as a pump or the like), a Venturi or the like. However, it will be understood that the mechanism by which the material may be transferred may vary depending on a number of factors, such as the type and composition of the material to be transferred, the distance the material needs to be transferred, and the like.

Any suitable type of container may be used that is substantially impervious to water and capable of containing the organic material slurry therein.

For example, the container may be a pot, a bucket, a barrel, a drum, a tank, an intermediate bulk container (IBC), a silo, a greenhouse, or the like.

The container may be configured to allow venting of gaseous materials.

In some embodiments, the container may be configured to allow bi-directional venting of gaseous materials. Bi-directional venting of gaseous materials may allow both an in-flow of gaseous materials into the container and an out-flow of gaseous material out of the container.

In some embodiments, the container may be configured for passive ventilation (such as by convection) or may be configured for mechanical ventilation (such as by forced airflow ventilation).

The organic material slurry may be exposed to a source of electromagnetic radiation during fermentation or may be fermented under conditions which block specific wavelengths of electromagnetic radiation. In a preferred embodiment of the invention, the fermentation conditions of the organic material slurry promote the capture of specific wavelengths of electromagnetic radiation. Preferably, the fermentation conditions of the organic material slurry promote the capture of non-visible radiation. In this instance, it will be understood that non-visible radiation comprises electromagnetic radiation having wavelengths that fall above and/or below visible light, that is, infrared light, violet or ultraviolet light, X-rays, radio waves, microwave, gamma rays and the like. Preferably, the fermentation conditions may promote activity of non-plant chlorophyll-based organisms and/or decreases activity of green and/or black sulphur bacteria. Advantageously, the method of the present invention results in fermentation of an organic material without requiring special environmental conditions.

The container for the fermentation of the organic material slurry may comprise an agitation means, wherein the agitation means periodically agitates the organic material slurry.

Any suitable agitation means may be used capable of turning over, aerating or otherwise mixing the organic material slurry.

In use, it is envisaged that agitating the organic material slurry may ensure sufficient contact between the process catalyst and the organic material slurry is achieved and/or assist in the aeration of the organic material slurry. Typically, however, the organic material slurry may be non-agitated. In use, it is envisaged that movement of organisms and/or convection currents within the slurry effectively homogenises the slurry.

In some embodiments, the fermentation process to produce an amended organic material may be conducted over a period of at least 1 day, at least 3 days, at least 7 days, at least 14 days, at least 21 days, or at least 28 days, preferably about 28 days.

In some embodiments, the process catalyst may be applied to the amended organic material to maintain the fermentation process, such that the amended organic material effectively undergoes a subsequent fermentation process.

In some embodiments, the subsequent fermentation process may be conducted over the same period of time as the preceding fermentation process, a shorter period of time, or a longer period of time. Typically, the period of time may be sufficient to reinitiate and/or maintain the fermentation process.

In some embodiments, the method for converting an organic material into a catalyst for biological hydrosynthesis comprises recovering a liquid from the amended organic material and transferring the liquid to a fermentation chamber.

In use, it is envisaged that the liquid recovered from the amended organic material may comprise a liquid by-product of a biological activity in and/or on the organic material slurry, a water by-product of a biological activity in and/or on the organic material slurry, excess liquid from the solid to liquid adjustment step, or a mixture thereof.

The liquid recovered from the amended organic material may be recovered by any suitable means.

Usually, the process is sufficient to separate the liquid from any residual solid material and/or floating biomass.

The container may comprise a collection portion (such as a reservoir) located in a lower portion of the container, wherein liquid may be collected and subsequently drained via an outlet portion of the container to recover the liquid from the amended organic material.

The outlet portion may be of any suitable type.

For example, the outlet portion may be a tap, a valve, a hose connector, a water tank adapter, a hose tail fitting, a tank outlet fitting, a bulkhead fitting, or the like.

In some embodiments, the container may comprise an outlet portion located in a lower portion thereof, wherein the amended organic material may be allowed to gravity drain or drain under vacuum and the liquid recovered from the container accordingly. In this instance, it is envisaged that the outlet portion may comprise a drain port or other aperture.

In further embodiments, the amended organic material may be dewatered using a mechanical dewatering process, such as a conveyor or screw press, a belt filter press, a chamber filter press, or the like.

In yet further embodiments, the amended organic material may be allowed to settle in the container such that the liquid component and the solid component separate, and the liquid decanted from the solid component. In this instance, it will be understood that the outlet portion of the container may be any portion of the container from which the liquid may be decanted. However, a person skilled in the art will appreciate that the type and location of the outlet portion may vary depending on a number of factors, such as the type of container, whether the fermentation process is a batch or continuous process, and the type of operation to recover the liquid.

In some embodiments, the liquid may be recovered from the fermentation of size-reduced organic material at any suitable point during the fermentation process. For example, the liquid may be recovered after at least 1 day, at least 3 days, at least 7 days, at least 14 days, at least 21 days, or at least 28 days of fermentation, preferably after about 28 days of fermentation.

The liquid recovered from the amended organic material may be used for any suitable purpose.

For example, the liquid recovered from the amended organic material may be used to adjust the solid to liquid ratio of the size-reduced organic material, may be used as a catalyst in a fermentation process, may be used to amend an organic material, may be used to amend a growth media, a site, a nutrient-depleted site, a contaminated site, in waste treatment, may be subjected to a fermentation process to produce an amended liquid, or any suitable combination thereof.

In use, it is envisaged that using the liquid recovered from the amended organic material to adjust the solid to liquid ratio of the size-reduced organic material may transfer a source of and/or substrates produced by and which stimulate the activity of at least one of an aerobic microorganism, an anaerobic microorganism, a heterotrophic microorganism and a photosynthetic microorganism between one or more containers comprising size-reduced organic material. In addition, by recirculating the liquid recovered from the amended organic material to the size-reduced organic material may cause the accumulation of beneficial organisms and/or substrates in and/or on the size-reduced organic material and/or liquid collection portion in the container.

In use, it is envisaged that after the liquid may be recovered from the amended organic material, the solid to liquid ratio of the amended organic material may be adjusted to re-form the organic material slurry. In this instance, it is envisaged that the process catalyst may be re-applied to the amended organic material to maintain the fermentation process.

Typically, the method for converting an organic material into a catalyst for biological hydrosynthesis may comprise the step of subjecting the liquid recovered from the amended organic material to a fermentation process to produce an amended liquid. Usually, the fermentation process includes undertaking an amendment of the liquid to produce an amended liquid with a balancing catalyst in the fermentation chamber, wherein the amended liquid is a catalyst for biological hydrosynthesis.

The balancing catalyst may be of any suitable type. Preferably, the balancing catalyst may foster the reaction activity of one or more prokaryotic organisms in the liquid recovered from the amended organic material. In some embodiments of the invention, the process catalyst and the balancing catalyst may be the same type of catalyst, or may be of different types. Preferably, the balancing catalyst comprises the process catalyst.

The balancing catalyst may be applied to the liquid recovered from the amended organic material in any suitable manner.

For example, the balancing catalyst may be sprayed onto the liquid, the balancing catalyst may be dispersed or blended into the liquid, the balancing catalyst may form a solution which is dispersed in the liquid, or any suitable combination thereof. However, a person skilled in the art will understand that the method of applying the balancing catalyst to the liquid recovered from the amended organic material may vary depending on a number of factors, such as the composition and characteristics of the balancing catalyst, the method of application, and the type and amount of the liquid to be amended.

The balancing catalyst may be applied at any suitable rate to the liquid recovered from the amended organic material.

For instance, the balancing catalyst may be applied at a rate of about 1 L per 1000 L, about 5 L per 1000 L, about 10 L per 1000 L, about 25 L per 1000 L, about 50 L per 1000 L, about 75 L per 1000 L, about 100 L per 1000 L, about 150 L per 1000 L, about 200 L per 1000 L, or even about 250 L per 1000 L of the liquid recovered from the amended organic material. Again, a person skilled in the art will appreciate that the application rate may vary depending on a number of factors, including the type and composition of the organic material, the percentage solid components in the liquid recovered from the amended organic material, and the method of application of the process catalyst. Typically, the balancing catalyst may be applied at a rate of about 15 L per 1000 L of recovered liquid.

The balancing catalyst may be mixed with one or more other substances before the balancing catalyst may be applied to the liquid.

Any suitable substance may be used.

For instance, the substance may act as a processing aid for storage and delivery of the catalyst, may facilitate the application of the catalyst to the liquid, may facilitate the liquid taking up the catalysts, may maintain viability of an organism in the catalyst, increase the available pool of a nutrient in the recovered liquid, may stimulate a targeted response in nutrient accumulation, or the like.

Any suitable additive may be used.

For instance, the additive may comprise an emulsifier, a stabiliser, a wetting agent, a preservative, a surfactant, a mineral, a source of a nutrient, or the like.

For instance, a source of calcium may be added to the catalyst to increase the available calcium in the liquid recovered from the amended organic material. In use, it is envisaged that the source of calcium assists in the adsorption of excess hydrogen in the liquid recovered from the amended organic material.

For instance, a source of sugar may be added to the catalyst to improve the fermentative capacity of the liquid recovered from the amended organic material.

In preferred embodiments, 0.5% v/v milk of lime or lime slurry may be added to the liquid recovered from the amended organic material.

In some embodiments, liquid from the fermentation of one or more batches of size-reduced organic material may be combined.

In some embodiments of the invention, the size-reduced organic material may have been fermented over the same period of time, or over different periods of time.

In some embodiments of the invention, the one or more batches of size-reduced organic material may comprise the same type of organic material, or different types.

In some embodiments, the fermentation process to produce an amended liquid may be conducted over a period of at least 1 day, at least 3 days, at least 7 days, at least 14 days, at least 21 days, or at least 28 days, preferably over a period of about 7 days.

In some embodiments, the balancing catalyst may be applied to the amended liquid to maintain the fermentation process, such that the amended liquid effectively undergoes a subsequent fermentation process.

In some embodiments, the subsequent fermentation process may be conducted over the same period of time as the first fermentation process, a shorter period of time, or a longer period of time. Typically, however the period of time may be sufficient to reinitiate and/or maintain the fermentation process, In some embodiments, amended liquid obtained from the fermentation of one or more batches of liquid recovered from the amended organic material may be combined.

In some embodiments, the one or more batches of the liquid may have been fermented over the same period of time, or over different periods of time. In some embodiments of the invention, the one or more batches of the liquid may have been obtained from the fermentation of the same type of organic material or from different types.

In use, it is envisaged that the amended liquid may comprise a source of and/or a substrate produced by and which stimulates the activity of the one or more prokaryotic organisms across the organic material.

In some embodiments, the amended liquid may be used to adjust the solid to liquid ratio of the size-reduced organic material. For example, the amended liquid may facilitate the transfer of a source of and/or a substrate produced by and which stimulates the activity of the one or more prokaryotic organisms across the organic material. It is envisaged that the migration of the liquid by capillary action through the organic material and/or the evapotranspiration of the liquid may facilitate the transfer of a source of and/or a substrate produced by and which stimulates the activity of the one or more prokaryotic organisms.

In use, it is envisaged that over time the recycling of the liquid through evapotranspiration and precipitation cycles may construct a matrix of biological energy generation points in and/or on the amended organic material capable of facilitating sustained energy generation and the generation of energy storage compounds, such as a humified soil, on the organic material.

Any of the features described herein can be combined in any combination with any one or more of the other features described herein within the scope of the invention.

The reference to any prior art in this specification is not, and should not be taken as an acknowledgement or any form of suggestion that the prior art forms part of the common general knowledge.

BRIEF DESCRIPTION OF DRAWINGS

Preferred features, embodiments and variations of the invention may be discerned from the following Detailed Description which provides sufficient information for those skilled in the art to perform the invention. The Detailed Description is not to be regarded as limiting the scope of the preceding Summary of Invention in any way. The Detailed Description will make reference to a number of drawings as follows:

FIG. 1 illustrates a flowchart of a method for converting an organic material into a catalyst for biological hydrosynthesis according to an embodiment of the present invention.

DETAILED DESCRIPTION

In FIG. 1, there is shown a flowchart of a method for converting an organic material into a catalyst for biological hydrosynthesis (100) according to an embodiment of the present invention.

An organic material comprising at least one source of readily available carbon, at least one complex carbon-containing compound and at least one source of protein is subjected to a size reduction process (10) to produce a size-reduced organic material. The organic material may be contacted with a preparatory catalyst before, during or after the size reduction process. Preferably, the organic material may be contacted with a preparatory catalyst through contact with equipment (such as macerators, agitators, containers, bins, buckets, conveyors, and the like) cleaned with the preparatory catalyst. In this instance, it will be understood that residual preparatory catalyst on the surface of the equipment may be transferred to the organic material during processing of the organic material.

The solid to liquid ratio of the size-reduced organic material is adjusted (12) to form an organic material slurry comprising at least about 25% to 30% solid components. The organic material slurry is then contacted with a process catalyst at a rate of about 15 L per 1000 L of organic material slurry and undergoes a fermentation process (14) over a period of about 28 days to produce an amended organic material.

The amended organic material undergoes a solid-liquid separation process (16) and the liquid recovered from the amended organic material is subsequently subjected to a fermentation process (18). The liquid is contacted with a balancing catalyst comprising a source of calcium at a rate of about 15 L per 1000 L of recovered liquid and fermented over a period of about 7 days to produce an amended liquid.

After the liquid is recovered from the solid-liquid separation process (16), the solid to liquid ratio of the amended organic material is re-adjusted to re-form an organic material slurry. The process catalyst may be re-applied to the amended organic material to maintain the fermentation process.

In the present specification and claims (if any), the word 'comprising' and its derivatives including 'comprises' and 'comprise' include each of the stated integers but does not exclude the inclusion of one or more further integers.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment. Furthermore, the particular features, structures, or characteristics may be combined in any suitable manner in one or more combinations.

In compliance with the statute, the invention has been described in language more or less specific to structural or methodical features. It is to be understood that the invention is not limited to specific features shown or described since the means herein described comprises preferred forms of putting the invention into effect. The invention is, therefore, claimed in any of its forms or modifications within the proper scope of the appended claims (if any) appropriately interpreted by those skilled in the art.

The invention claimed is:

1. A method for converting an organic material into a catalyst for biological hydrosynthesis, the method comprising the steps of:
    providing an organic material comprising at least one source of readily available carbon, at least one complex carbon-containing compound and at least one source of protein;
    contacting the organic material with a preparatory catalyst;
    subjecting the organic material to a size reduction process to produce a size-reduced organic material;
    adjusting a solid to liquid ratio of the size-reduced organic material to form an organic material slurry;
    subjecting the organic material slurry to a fermentation process to produce an amended organic material, by applying a process catalyst to at least a portion of the organic material slurry;
    recovering a liquid from the amended organic material and transferring the liquid recovered to a fermentation chamber; and
    subjecting the liquid recovered to a fermentation process to produce an amended liquid by applying a balancing catalyst to the liquid recovered in the fermentation chamber,
    wherein the amended liquid is a catalyst for biological hydrosynthesis.

2. A method for converting an organic material into a catalyst for biological hydrosynthesis according to claim 1, comprising contacting the organic material with the preparatory catalyst through contact with equipment cleaned with the preparatory catalyst.

3. A method for converting an organic material into a catalyst for biological hydrosynthesis according to claim 2, wherein the preparatory catalyst removes residual materials from a surface of the equipment and controls proliferation of competitive fermentative or putrescent microbial activity in and around the method.

4. A method for converting an organic material into a catalyst for biological hydrosynthesis according to claim 1, wherein the preparatory catalyst comprises an essential oil or extract.

5. A method for converting an organic material into a catalyst for biological hydrosynthesis according to claim 1, wherein the solid to liquid ratio of the size-reduced organic material is at least about 25% solid components.

6. A method for converting an organic material into a catalyst for biological hydrosynthesis according to claim 1, comprising adding the process catalyst to the size-reduced organic material before, during or after the size reduction process.

7. A method for converting an organic material into a catalyst for biological hydrosynthesis according to claim 1, comprising adding the process catalyst to the size-reduced organic material during the size reduction process.

8. A method for converting an organic material into a catalyst for biological hydrosynthesis according to claim 1, wherein the process catalyst has a capacity to capture non-visible radiation.

9. A method for converting an organic material into a catalyst for biological hydrosynthesis according to claim 1, further comprising a step of adjusting a solid to liquid ratio of the amended organic material after the liquid is recovered to re-form the organic material slurry.

10. A method for converting an organic material into a catalyst for biological hydrosynthesis according to claim 9, comprising applying at least one of the preparatory catalyst or the process catalyst to the amended organic material to maintain the fermentation process.

11. A method for converting an organic material into a catalyst for biological hydrosynthesis according to claim 1, wherein the balancing catalyst comprises the process catalyst and a source of calcium.

12. A method for converting an organic material into a catalyst for biological hydrosynthesis according to claim 1, comprising performing the method in two or more batch processes, each of the two or more batch processes generating the amended liquid.

13. A method for converting an organic material into a catalyst for biological hydrosynthesis according to claim 12, comprising combining the amended liquid generated from each of the two or more batch processes.

14. A method for converting an organic material into a catalyst for biological hydrosynthesis according to claim 1, further comprising applying the balancing catalyst to the amended liquid to maintain the fermentation process, such that the amended liquid effectively undergoes a subsequent fermentation process.

15. A method for converting an organic material into a catalyst for biological hydrosynthesis according to claim 1, wherein the at least one source of readily available carbon is at least partially sourced from an amended organic material.

16. A catalyst for biological hydrosynthesis obtained from the method according to claim 1.

\* \* \* \* \*